US006810281B2

(12) United States Patent
Brock et al.

(10) Patent No.: US 6,810,281 B2
(45) Date of Patent: Oct. 26, 2004

(54) MEDICAL MAPPING SYSTEM (75) Inventors: David L. Brock, Natick, MA (US); Gary Rogers, Wenham, MA (US)

(73) Assignee: endoVia Medical, Inc., Norwood, MA (US)

(*) Notice: Subject to any disclaimer, the term of this patent is extended or adjusted under 35 U.S.C. 154(b) by 13 days.

(21) Appl. No.: 10/034,871

(22) Filed: Dec. 21, 2001

(65) Prior Publication Data

US 2002/0120188 A1 Aug. 29, 2002

Related U.S. Application Data (63) Continuation-in-part of application No. 10/011,449, filed on Nov. 16, 2001, and a continuation-in-part of application No. 10/011,450, filed on Nov. 16, 2001.
(60) Provisional application No. 60/257,816, filed on Dec. 21, 2000.

(51) Int. Cl.[7] ................................................. A61B 5/00
(52) U.S. Cl. ........................ 600/427; 600/407; 600/436; 600/473; 600/549
(58) Field of Search ................................ 600/102, 407, 600/410, 424, 427, 436, 473, 549; 606/130

(56) References Cited

U.S. PATENT DOCUMENTS

| | | | |
|---|---|---|---|
| 4,654,024 A | | 3/1987 | Crittenden et al. |
| 4,977,886 A | | 12/1990 | Takehana et al. |
| 5,052,402 A | | 10/1991 | Bencini et al. |
| 5,084,054 A | | 1/1992 | Bencini et al. |
| 5,151,856 A | * | 9/1992 | Halmann et al. ........... 600/508 |
| 5,172,700 A | | 12/1992 | Bencini et al. |
| 5,217,003 A | | 6/1993 | Wilk |
| 5,238,002 A | | 8/1993 | Devlin et al. |
| 5,238,005 A | | 8/1993 | Imran |
| 5,271,381 A | | 12/1993 | Ailenger et al. |
| 5,287,861 A | | 2/1994 | Wilk |
| 5,339,799 A | | 8/1994 | Kami et al. |
| 5,347,987 A | | 9/1994 | Feldstein et al. |

(List continued on next page.)

FOREIGN PATENT DOCUMENTS

| | | |
|---|---|---|
| EP | 0776738 A2 | 6/1997 |
| WO | WO98/25666 | 6/1998 |
| WO | WO00/60521 | 10/2000 |

OTHER PUBLICATIONS

Ikuta, et al., "Shape Memory Alloy Servo Actuator System With Electric Resistance Feedback And Application For Active Endoscope", 1988 IEEE, CH2555–1/88/0000/0427–430.

M.W. Thring, "Robots and Telechirs: Manipulators With Memory; Remote Manipulators; Machine Limbs For the Hanidcapped", First published in 1983 by Ellis Horwood Limited.

*Primary Examiner*—Ruth S. Smith
(74) *Attorney, Agent, or Firm*—Hamilton, Brook, Smith & Reynolds, P.C.

(57) ABSTRACT

Apparatus and method for sensing at an anatomic body site and mapping or transforming the sensor signal into various forms of virtual image and feedback signals, having particular application in assisting surgeons and other operators during a medical procedure. In one embodiment, a medical system is provided that includes a medical implement, a manipulator controllable by an operator for control of the medical implement at an anatomic body site and a sensing device for sensing a non-visible field associated with a body structure at the site. A controller, intercoupling the sensing device and the manipulator, includes a mapping component for translating characteristics of the sensed field signal into a tactile feedback signal to the manipulator to warn the surgeon that he is approaching this structure with the implement. Alternatively or in addition, a virtual image of the body structure is displayed, separate or preferably together with a visual image of the site, to assist a surgeon in manipulating a medical implement.

13 Claims, 5 Drawing Sheets

U.S. PATENT DOCUMENTS

| | | |
|---|---|---|
| 5,350,355 A | 9/1994 | Sklar |
| 5,409,019 A | 4/1995 | Wilk |
| 5,429,144 A | 7/1995 | Wilk |
| 5,480,422 A * | 1/1996 | Ben-Haim ................ 607/122 |
| 5,497,784 A | 3/1996 | Imran |
| 5,515,478 A | 5/1996 | Wang |
| 5,520,644 A | 5/1996 | Imran |
| 5,524,180 A | 6/1996 | Wang et al. |
| 5,618,294 A | 4/1997 | Aust et al. |
| 5,624,398 A | 4/1997 | Smith et al. |
| 5,626,553 A | 5/1997 | Frassica et al. |
| 5,626,595 A | 5/1997 | Sklar et al. |
| 5,632,758 A | 5/1997 | Sklar |
| 5,667,476 A | 9/1997 | Frassica et al. |
| 5,762,458 A | 6/1998 | Wang et al. |
| 5,792,135 A | 8/1998 | Madhani et al. |
| 5,807,377 A | 9/1998 | Madhani et al. |
| 5,808,665 A | 9/1998 | Green |
| 5,814,038 A | 9/1998 | Jensen et al. |
| 5,815,640 A | 9/1998 | Wang et al. |
| 5,823,993 A | 10/1998 | Lemelson |
| 5,845,646 A | 12/1998 | Lemelson |
| 5,855,583 A | 1/1999 | Wang et al. |
| 5,861,024 A | 1/1999 | Rashidi |
| 5,876,325 A | 3/1999 | Mizuno et al. |
| 5,878,193 A | 3/1999 | Wang et al. |
| 5,907,664 A | 5/1999 | Wang et al. |
| 5,928,248 A | 7/1999 | Acker |
| 5,954,692 A | 9/1999 | Smith et al. |
| 5,964,717 A | 10/1999 | Gottlieb et al. |
| 5,976,122 A | 11/1999 | Madhani et al. |
| 6,001,108 A | 12/1999 | Wang et al. |
| 6,007,550 A | 12/1999 | Wang et al. |
| 6,007,560 A | 12/1999 | Gottlieb et al. |
| 6,024,695 A | 2/2000 | Taylor et al. |
| 6,058,323 A | 5/2000 | Lemelson |
| 6,063,095 A | 5/2000 | Wang et al. |
| 6,080,181 A | 6/2000 | Jensen et al. |
| 6,096,004 A | 8/2000 | Meglan et al. |
| 6,120,433 A | 9/2000 | Mizuno et al. |
| 6,132,368 A | 10/2000 | Cooper |
| 6,197,017 B1 | 3/2001 | Brock et al. |
| 6,223,100 B1 | 4/2001 | Green |

* cited by examiner

MEDICAL MAPPING SYSTEM

RELATED APPLICATIONS

This application is a continuation-in-part of and claims the benefit of priority of U.S. Provisional Application Ser. No. 60/257,816, filed Dec. 21, 2000.

U.S. application Ser. No. 10/011,449, filed Nov. 16, 2001; and

U.S. application Ser. No. 10/011,450, filed Nov. 16, 2001 each of which are hereby incorporated by reference in their entirety.

FIELD OF THE INVENTION

The present invention relates in general to a mapping system and method useful for mapping identifying anatomic members such as tissues, nerves, vessels or any other anatomic body part. This mapping can assist in the manipulation of a medical instrument, catheter, or the like, either under direct or robotic control.

BACKGROUND OF THE INVENTION

Part of the "art" of surgery is knowing where to cut and where the "danger zones" are located. The surgeon relies on visual clues to determine where important anatomical structures are located. He also relies upon palpation. Landmarks such as bony prominence, ligament insertions, position of muscles and solid organs, and other landmarks guide the surgeon during tissue dissection (also referred to as transection).

One of the major complications of surgery is inadvertent transection of sensory nerves, motor nerves, arteries, veins and hollow viscus. In most cases this occurs when key structures are poorly visualized by the surgeon, or due to inexperience or altered anatomical structures (e.g., surgical landrnarks). Blunt dissection is performed either manually using the fingers or using an instrument, and sharp dissection is performed using a scissors, electrical-surgical device, or scalpel.

A common side effect or complication of much surgery is neurological trauma, paresis or permanent paralysis occasioned by the severing of nerves. Over 5% of major head and neck surgeries (e.g., parotidectomy) result in damage to the facial nerve resulting in weakness of the facial muscles or partial paralysis of the face. A frequent consequence of prostate surgery is damage to the sacral nerves, which control erectile function and ejaculation. Almost 40% of men undergoing prostatectomy are left impotent or have significant problems with erectile function.

Inadvertent perforation of the aorta, or of the superior or inferior Vena Cava, can cause a major hemorrhage which may result in death. The Vena Cava may be ruptured during dissection of the spleen or resection of tissues on the posterior surface of the liver. Transection of smaller arteries and veins, while less life-threatening, are a cause of significant morbidity, often require transfuision to compensate for blood loss, and can significantly increase the length of hospitalization following a procedure. Similarly, transection of the ureter results in major morbidity, requires multiple operations to correct, may result in renal failure and significantly impairs quality of life. Perforation of other hollow viscus, such as the bowel or bladder wall, may result in peritonitis and death.

Electrical transducers are commonly used in medical practice to measure electrical impulses within nerve bundles. These instruments include: electroencephalograms (EEG), electrocardiogram (EKG), electromyography (EMG), and others. All these devices have in common the ability to measure electrical impulses generated by nerve structures. The electrical fields vary with motor nerve, sensory nerve, the degree of myelinization and the number of nerves in the particular neural bundle. The electrical impulses are typically in the form of a waveform that is examined and interpreted by a surgeon or physician. Such a readout is primarily used as a diagnostic tool in determining irregularities in organs such as the heart or brain.

Subtle temperature variations also exist within different anatomical compartments. Venous blood returning from an extremity is cooler than arterial blood. Sites of infection tend to be slightly warmer than healthy tissues. Abscess pockets tend to be somewhat cooler than surrounding tissues. These temperature variations are generally below the threshold of human proprioception. The variations can be less than a tenth of a degree. A number of different thermistors, which can measure temperature variation to a hundredth of a degree, are used in medicine to monitor vital signs, cardiac output, and other functions. Again, such use is primarily diagnostic.

Gallium and technetium, as well as other isotopes, are used for tracking infection, lymphatic drainage and to provide contrast during magnetic resonance imaging (MRI) These isotopes are gamma emitters and, in general patients undergoing these scans are evaluated by gamma counters which then measure the degree of radioactive uptake. This data is then graphically displayed as an x-ray film.

During sentinel node biopsy, lymphoscintigraphy is used to localize the regional draining nodal basin in breast cancer and melanoma therapy. A small incision is then made in the skin overlying the "hot" node. Blunt and sharp dissection is used to reach the nodal basin. A sterile-wrapped Geiger counter is then inserted into the wound to identify the affected node(s). Further dissection and Geiger counter testing is performed until the radioactive sites are fully identified and resected. This is a time-consuming and laborious process, with the operative field landmarks and lymph nodes shifting in space with each insertion/removal of instruments.

In these various techniques, there is a need for a better method of identifying anatomic structures or parts, particularly when these structures or parts are not visible to the surgeon's eye. By identifying these structures or parts, one can avoid the aforementioned problems that can lead to tissue, organ, or nerve damage, paresis, permanent paralysis, or other injuries that impair the quality of life of the patient.

SUMMARY OF THE INVENTION

In one embodiment, what is sensed is a non-visible field and what is provided is a combined display of virtual and visual images. In this embodiment, a system is provided for generating the display of a body structure. The system includes a sensor positionable at an internal body site for sensing a non-visible field of a body structure at the site and generating a sensor signal indicative of the field. A transformation system transforms the sensor signal into virtual image data. A source of visual image data for the site is also provided. A visual system enables combined display of the visual image data and the virtual image data.

According to a corresponding method, steps are provided for sensing at an internal body site a non-visible field of a body structure at the site and generating a sensed signal indicative of the field, transforming the sensed signal into virtual image data, providing visual image data for the site, and displaying in combination the visual image data and the virtual image data.

In another embodiment, what is sensed is a non-visible field by a sensor positioned with a computer-controlled instrument, and what is provided is virtual image data. In this embodiment, a system is provided for obtaining virtual image data of a body structure. The system includes a computer-controlled instrument for positioning a sensor at an internal body site, the sensor sensing a non-visible field of a body structure at the site and generating a sensor signal indicative of the site, and a transformation system is provided for transforming the sensor signal into virtual image data.

According to a corresponding method, steps are provided for positioning by computer control a sensor at an internal body site, sensing a non-visible field of a body structure at the site and generating a sensor signal indicative of the field, and transforming the sensor signal into virtual image data.

In another embodiment, what is sensed is a non-visible field and what is provided is a tactile feedback for controlling manipulation of a medical implement. In accordance with this embodiment, a system is provided for controlling manipulation of a medical implement including a sensor positionable at an internal body site for sensing a non-visible field of a body structure at the site and generating a sensor signal indicative of the field, a transformation system for transforming the sensor signal into a feedback signal, and a control system, including a haptic user interface, for manipulating a medical implement at the site, the control system receiving the feedback signal and in response thereto providing a tactile signal at the user interface.

In accordance with the corresponding method, there are steps provided for sensing a non-visible field of a body structure at an internal body site and generating a sensed signal indicative of the field, transforming the sensed signal into a feedback signal, and utilizing the feedback signal to provide a tactile signal at a haptic user interface for controlling manipulation of a medical implement at the site.

In another embodiment, what is sensed is a visual image and what is provided is a tactile feedback for controlling manipulation of a medical implement. In accordance with this embodiment, a system is provided for controlling manipulation of a medical implement including a sensor positionable at an internal body site for sensing a visual image of a body structure at the site and generating a sensor signal indicative of the image, a transformation system for transforming the sensor signal into a feedback signal, and a control system, including a haptic user interface, for manipulating a medical implement at the site, the control system receiving the feedback signal and in response thereto providing a tactile signal at the user interface.

In accordance with the corresponding method, there are steps provided for sensing a visual image of a body structure at an internal body site and generating a sensed signal indicative of the image, transforming the sensed signal into a feedback signal, and utilizing the feedback signal to provide a tactile signal at a haptic user interface for controlling manipulation of a medical implement at the site.

ADDITIONAL EMBODIMENTS

Various aspects of the present invention are described herein in a number of different embodiments. Many of these embodiments relate to a mapping system and method for identifying the location of certain anatomic areas such as, but not limited to, nerves or nerve bundles. This mapping involves the translation of certain sensed parameters (also referred to as stimuli) into response parameters. The sensed parameters include non-visible data (electromagnetic, thermal, infra-red, radioactive, etc.), and in other embodiments visible data and/or force sensed data. The response parameters include a display device, an audible device, a vibratory device and force feedback to a haptic interface.

Identification of the anatomic area may be used for the purpose of avoiding the area (such as in guiding a tissue dissection), or for the purpose of targeting, locating or guiding toward the anatomic area. Also, the identification may be employed in either a robotic system or a non-robotic system (e.g., in association with a hand-held instrument, such as a laparoscopic instrurnent). A telerobotic system usually is comprised of master and slave stations including, on the master side, a haptic interface and a display device, and, of the slave side, a controllable medical implement. Here a sensor is provided on the slave side, at the anatomic site of interest. The sensor detects, inter alia, electric, thermal, infra-red and radioactive fields, and is preferably, but not necessarily, carried at the distal end of the medical implement. The sensing may be by manual scanning or may be under computer control. Furthermore, the sensing may be either to establish a database, particularly for mapping non-visible fields to a display, or may be used in a real time mode, particularly for feedback control to the master haptic interface.

One aspect of the present invention is to provide, in addition to a visual image of an anatomic site of interest, a virtual image or boundary of an invisible (also referred to as non-visible) anatomic structure at the site, such as nerves or nerve bundles. The virtual image or boundary may be established by sensing, for example, an electric field, thermal field, or radioactive field associated with the anatomic structure. The sensed field may also be used in "real time" to control, for example, a haptic (relating to or based on the sense of touch) interface by providing tactile feedback to the surgeon regarding the hidden anatomic structure.

In accordance with one aspect of the invention there is provided a system for sensing a non-visible field to provide a tactile feedback to a haptic interface. This system may include a surgical implement, including for example an end effector or tool, to perform a predetermined surgical procedure at an anatomic body site. A controller is disposed between the surgical implement and the haptic interface and a sensor preferably, but not necessarily carried by the end effector, for sensing a non-visible field at the body site. The controller is responsive to manipulations at the haptic interface by an operator to control the surgical implement in performing the surgical procedure. The controller also is responsive to a feedback signal which is a function of a sensed parameter of the non-visible field. This signal is fed back to the haptic interface to provide a tactile indication to the operator as to the location of the anatomic structure that generated the field.

In accordance with various aspects of the present invention, a non-visible field may comprise an electrical field, a thermal field, a radio-active field, or an IR field. Also, considered as falling within the scope of the present invention are any other no-visible fields. Generally speaking, by the term "non-visible" reference is being made to a particular field established in the anatomy, either inherent or via stimulation, and that is not observable by the surgeon by the naked eye, such as by way of an endoscope. A "field" refers to a series of data points sensed over a particular area and representative of such parameters as electric field, temperature, or radio-activity. A "field" may also be identified as directly sensed or inferred sensory information which constructs a data set of values.

"Non-contact" as used in connection with haptic feedback control refers to non-visible as well as other types of sensed effects that are not based upon direct physical contact between the sensor and the anatomic member or part.

In accordance with various aspects of the invention, the sensed or predetermined parameter may comprise a magnitude of the field. Also, the sensor may be a voltmeter, thermistor, gamma detector, IR detector, or any other type of sensing device that would sense the particular non-visible field. The aforementioned anatomic body member may comprise a nerve or nerve bundle, vascular vessels, or virtually any other body part.

In accordance with still another aspect of the invention, there may be provided a stimulator for stimulating the anatomic body member. The stimulator may be controlled from the controller so as to emit a predefined electrical stimulation signal that is coupled to energize the body member. The detected stimulation signal is fed back to the controller to identify the body member based upon a recognizable pattern. The pattern may be a repetitive pattern establishing an anatomic body member signature.

In accordance with another aspect of the invention, the system may include a display, which may be coupled with an optic element, for display the area at the anatomic body site. A controller receives a signal from the sensor and establishes on the display a map of the field (a virtual boundary defined by the map) about an anatomic body member. Moving the sensor to a plurality of locations in juxtaposition to the anatomic body member generates a map including boundaries of the field relative to the anatomic body site. The display is observable by the surgeon for displaying both a visual image and a virtual image, the virtual image being representative of the map boundaries and essentially representative of the position of the non-visible field.

In accordance with another aspect of the invention, there is provided a medical system comprising a surgical implement including an end effector used to carry out a predetermined surgical procedure at an anatomic body site, a sensor for sensing a non-visible field that is established associated with a member at the anatomic body site, and a display. Further included is a controller for receiving signals from the sensor and establishing a map of the field about the member at the anatomic body site. The controller couples to the display and establishes on the display both a visual image of the area at the anatomic body site as well as a virtual image representative of a boundary defined by the map and thus defined by the non-visible field.

In accordance with another aspect of the invention, there may also be provided a haptic interface for control of the surgical implement. A controller coupled to the haptic interface controls an operator's action at the haptic interface as a function of a predetermined parameter of the non-visible field.

In accordance with another aspect of the invention, there is provided a telerobotic surgery system having a slave station at which a surgical implement is disposed and a master station with a surgeon interface at which manipulations occur to control the surgical implement. Apparatus is provided for sensing a non-visible field associated with an anatomic body member in which the non-visible field distinguishes the anatomic body member from the surrounding area. The apparatus can be used for generating a tactile feedback signal at the surgeon interface. Such apparatus may comprise a sensor carried by the surgical implement for detecting the non-visible field generated from the anatomic body member. Also included is a controller coupled from the sensor, responsive to the magnitude of the field, for feeding back to the master station a control signal to the surgeon interface so as to provide a tactile response to the surgeon based upon the magnitude of the detected field.

In accordance with another aspect of the invention, there is provided a telerobotic surgery system having a slave station at which a surgical implement is disposed and a master station with a surgeon interface at which manipulations occur to control the surgical implement. An apparatus is provided for mapping a non-visible field associated with an anatomic body part and in which the non-visible field distinguishes the anatomic body part from other anatomic structures. This apparatus includes a sensor for detecting the non-visible field generated from the anatomic body part, a controller coupled from the sensor, responsive to the disposition of the sensor at a plurality of locations in juxtaposition to the anatomic body part, to generate a map including boundaries of the field relative to other anatomic body structures, and a display (coupled to the controller) observable by the surgeon for displaying both a visual image of the area about the anatomic body part as well as a virtual image representative of the map boundaries.

In accordance with another aspect of the invention, there is provided a medical device that comprises a surgical implement having an end effector used to carry out a predetermined surgical procedure at an anatomic body site that includes an anatomic body member that is not visible to the surgeon. The medical device includes a handle member operated so as to control the surgical implement and end effector, a sensor for detecting a non-visible field that is associated with the anatomic body member and that demarcates a boundary of the field of the anatomic body member, and a controller coupled from and responsive to the sensor for providing at the handle a tactile indication to the surgeon based on a predetermined parameter of the field.

In accordance with another aspect of the invention, there is provided a medical system useful in identifying an internal anatomic body member that is not visible to the surgeon by direct or indirect optical means. This system enables improved control by the surgeon of certain surgical procedures. The system comprises a sensor for sensing a non-visible field that is associated with an anatomic body member. By way of example, this non-visible field may be an electrical field about a nerve or nerve bundle. A controller is employed coupled from the sensor and responsive to signals representative of different locations of sensing relative to the anatomic body member so as to establish a map including boundaries of the field relative to other juxtapositioned anatomic structures. A display, observable by the surgeon, is coupled to the controller for visually displaying the virtual field boundaries based upon the non-visible field.

In accordance with still another aspect of the invention, there is provided a method of tactile feedback to a surgeon. This method includes disposing a medical implement at an anatomic body site in a position to effect, by a manipulator, a predetermined medical procedure. Next is a step of sensing a non-visible field associated with an anatomic body member which distinguishes the anatomic body member from the surrounding area at the anatomic body site. Lastly, is a step of generating a tactile feedback signal to the manipulator based upon a parameter of the non-visible field. This method may also include a step of stimulating the anatomic body member; this stimulation may include emitting a predefined electrical stimulation signal coupled to energize the anatomic body member.

In accordance with a further aspect of the invention, there is provided a method of identifying an internal anatomic body member that is not visible to a surgeon by direct optical means so as to enable improved control by the surgeon of a surgical procedure. This method includes sensing a non-visible field that is established and associated with the anatomic body member and controlling the sensing so as to be responsive to signals representative of different locations of sensing relative to the anatomic body member. This sensing establishes a map including virtual boundaries of the sensed field relative to other juxtapositioned anatomic structures. Last is the step of displaying, on a display, observable by the surgeon, the anatomic body site as well as the virtual field boundaries. This method may also include stimulating the anatomic body member.

In accordance with still another aspect of the invention, there is provided a medical system that comprises a sensing device for obtaining a visual image of an anatomic body site, a medical implement and a manipulator controlled by an operator for control of the implement at the anatomic body site. A controller intercouples the sensing device and the manipulator and includes a mapping component for translating predetermined characteristics of the visual image into a signal for controlling action at the manipulator.

In accordance with further aspects of this medical system, the signal for controlling action at the manipulator may comprise a force signal or a vibration signal. The sensing device may comprise an endoscope. The controller may control actions at the manipulator as a function of the position of the surgical implement within the anatomic body site. The surgical implement may comprise a surgical instrument with an end effector or a catheter or any other type of surgical implement. The manipulator may include a hand-held instrument or may comprise a haptic interface of a tele-robotic system.

In accordance with another aspect of the invention, there is provided a medical system that comprises a sensing device for obtaining a visual image of an anatomic body site, a surgical implement, and a manipulator controlled by a surgeon for control of the surgical implement at the anatomic body site. An audible device is employed in the system along with a controller intercoupling the sensing device and the audible device. This controller includes a mapping component for translating predetermined characteristics of the visual image into a signal for controlling the audible device.

In accordance with further aspects of the invention, the predetermined characteristics may represent an outline of an anatomic body member. The controller may control the audible device as a function of the position of the surgical implement within the anatomic body site and relative to the anatomic body member. The audible device is sounded when the surgical implement comes within a predefined proximity to the anatomic body member, so as to signal that the surgical implement is too close to the anatomic body member.

In accordance with still another aspect of the invention, there is provided a medical system that comprises a surgical implement, a manipulator, controlled by an operator for control of the surgical implement at an anatomic body site, and a force sensor for detecting by a direct contact a force imposed on the surgical implement at the anatomic body site. Also included is a visual display observable by the operator as well as a controller intercoupling the force sensor and the visual display and including a mapping block for translating predetermined characteristics from the force sensor into a signal for controlling the content of display on the visual display.

In accordance with further aspects of the invention, the controller controls the display content as a function of the position of the surgical implement within the anatomic body site. The force sensor may be carried directly on the surgical implement or may be at some other defined location relative to the surgical implement. The controller is responsive to a force signal from the force sensor for highlighting an area of the visual display corresponding to a location of the surgical implement. The highlighting may also include providing an indicia on the visual display representative of an area where a force of greater than a predetermined threshold force is sensed.

In accordance with a further aspects of the invention, there is provided a medical system that comprises a surgical implement, a manipulator controlled by an operator for control of the surgical implement at an anatomic body site, and a force sensor for detecting by direct contact a force imposed on the surgical implement at the anatomic body site. Also included in the system is a controller intercoupling the force sensor and the manipulator and including a mapping block for translating predetermined characteristics from the force sensor into a signal for controlling vibration at the manipulator.

In accordance with further aspects of this system, the controller controls the manipulator as a function of the position of the surgical implement within the anatomic body site. The force sensor may be carried by the surgical implement or may be at another location. The controller is responsive to a force signal from the force sensor for controlling the manipulator as a function of the measured force level.

In accordance with a further aspect of the invention, there is provided a medical system that comprises a surgical implement, a manipulator controlled by an operator for control of the surgical implement at an body site and a force sensor for detecting by direct contact a force imposed on the surgical implement at the body site. Also included in the system is an audible device and a controller for intercoupling the force sensor and the audible device and including a mapping component for translating predetermined characteristics from the force sensor into a signal for controlling the audible device.

In accordance with further aspects of this system, the controller is responsive to a force signal from the force sensor for controlling the magnitude of an audible signal from an audible device as a function of the magnitude of the force signal. The audible signal may be generated only when the force signal exceeds a preselected threshold.

In accordance with another aspect of the invention, there is provided a medical system comprising a surgical implement, a manipulator controlled by an operator for control of the surgical implement at an anatomic body site and a sensing device for sensing a non-visible field generated from an anatomic body member disposed at the anatomic body site. The system also includes a visual display and a controller intercoupling the sensing device and the visual display and including a mapping component for translating predetermined characteristics of the non-visible field from the sensing device into a signal for controlling the content on the visual display.

In accordance with other aspects of the above system, the manipulator intercouples with the controller and the controller is responsive to actions at the manipulator to control the surgical implement in carrying out a surgical procedure. The controller may establish on the display both a visual image of the area at the anatomic body site as well as a virtual image representative of a boundary defined by the mapping component and relating to the non-visible field. The non-visible field may be an electric field (which as used herein includes an electromagnetic field), a thermal field, a radioactive field, an IR field, or any other type of non-visible field.

In accordance with the various systems of the invention, the sensing device may comprise a voltmeter, a thermistor, a gamma counter, an IR detector or any other type of field detecting device. Also, a further sensing device may be used for obtaining a visual image of the anatomic body site wherein the controller translates predetermined characteristics of the visual image into a signal for controlling actions at the manipulator. The signal for controlling action at the manipulator may comprise a vibration signal. Also, an audible device may be employed wherein the controller translates predetermined characteristics of the visual image into a signal for controlling the audible device. The aforementioned system may also include a force sensor for detecting by direct contact a force imposed on the surgical implement at the anatomic body site. The controller may translate predetermined characteristics of the force signal into a signal for controlling the content on the visual display. The controller may translate predetermined characteristics of the force sensor into a signal for controlling vibration at the manipulator. If an audible device is employed, the controller may translate predetermined characteristics from the force sensor into a signal for controlling the audible device.

In accordance with another aspect of the invention, there is provided a medical system that comprises a medical implement, a manipulator controlled by an operator for control of the medical implement at an anatomical body site, and a sensing device for sensing a non-contact field generated from an anatomic body member disposed within the anatomic body site. A controller intercouples the medical implement, manipulator and sensing device and includes a mapping component for translating predetermined characteristics of the non-contact field from the sensing device to a signal for controlling actions at the manipulator.

In accordance with further aspects of this system, the signal for controlling action may control a tactile feedback to the operator. The signal for controlling actions may control a vibration level at the manipulator and there may also be provided a second sensing device for obtaining a visual image at the anatomic body site. This may include an endoscope.

In accordance with still a further aspect of the invention, there is provided a medical system that comprises a surgical implement for carrying out a predetermined surgical procedure at an anatomic body site, a sensing device for sensing a non-visible field generated from an anatomic body member disposed within the anatomic body site, and an audible device. A controller intercouples the sensing device and the audible device and includes a mapping component for translating predetermined characteristics from the sensing device into a signal for controlling the audible device. A manipulator may be provided for controlling the surgical implement at the anatomic body site. The controller is responsive to the magnitude of the sensed field for controlling the audible signal from the audible device as a function of the magnitude of the sensed field.

Numerous other features of the present invention should now become apparent upon a reading of the following detailed description:

DETAILED DESCRIPTION

Visual displays have been used extensively in connection with surgical procedures. However, these displays do not depict invisible or non-visible fields associated with a particular anatomic body structure of interest. One embodiment of the present invention identifies these non-visible fields so as to provide feedback to a surgeon interface. Electrical, thermal, radioactive, IR and other non-visible fields that surround tissues or that are associated with other anatomic structures, are sensed with an appropriate sensor. The sensor may be disposed at a distal end of an instrument. The sensor may be employed in a robotic system or in association with a hand-held instrument, such as a laparascopic instrument.

The term "invisible field" or "non-visible field" refers to a measurable parameter, but one that is not discernable to the naked eye by a surgeon, physician, or operator, such as through the traditional use of an endoscopic camera at an anatomic site. Although important embodiments of the invention relate to sensed "non-visible" fields, it is understood that other aspects of the invention extend to sensing of visible and/or force sensed data.

A signal from a sensing device may be amplified and preferably is transduced into a digital signal. With a controller, the digital signal can be mapped to, for example, a tactile feedback (palpable hardness or vibration sense) provided at a surgeon's tactile (haptic) interface.

In accordance with another aspect of the invention, successive digital signals may be stored to establish a database corresponding to an anatomic body area. The stored data may be used for establishing a virtual image or boundary on a display device for identifying, on the display device, the anatomic member that has generated the sensed field. In essence, the virtual image or boundary may be overlayed on a visible image to identify to the surgeon an invisible anatomic body member, such as a hidden nerve or nerve bundle.

In association with electrical (which as used herein is meant to include electromagnetic) fields, these electrical potentials, dipoles, and/or ionic currents that surround nerves can be measured using millivoltmeters. These meters may be embedded in a distal tip of an instrument, such as the tip of a robotic finger. In this way, differing electrical forces and dipoles can be mapped and then provided to the surgeon as different degrees of hardness/softness, or vibration. The surgeon is thus able to "feel" subtle electrical potentials, dipoles and ionic currents. Because these electrical fields are generally associated with nerves or nerve bundles, the surgeon is essentially able to determine the position of these nerves or nerve bundles even though they are not visible to the surgeon through a conventional optical system, such as an endoscope.

Figure 6:
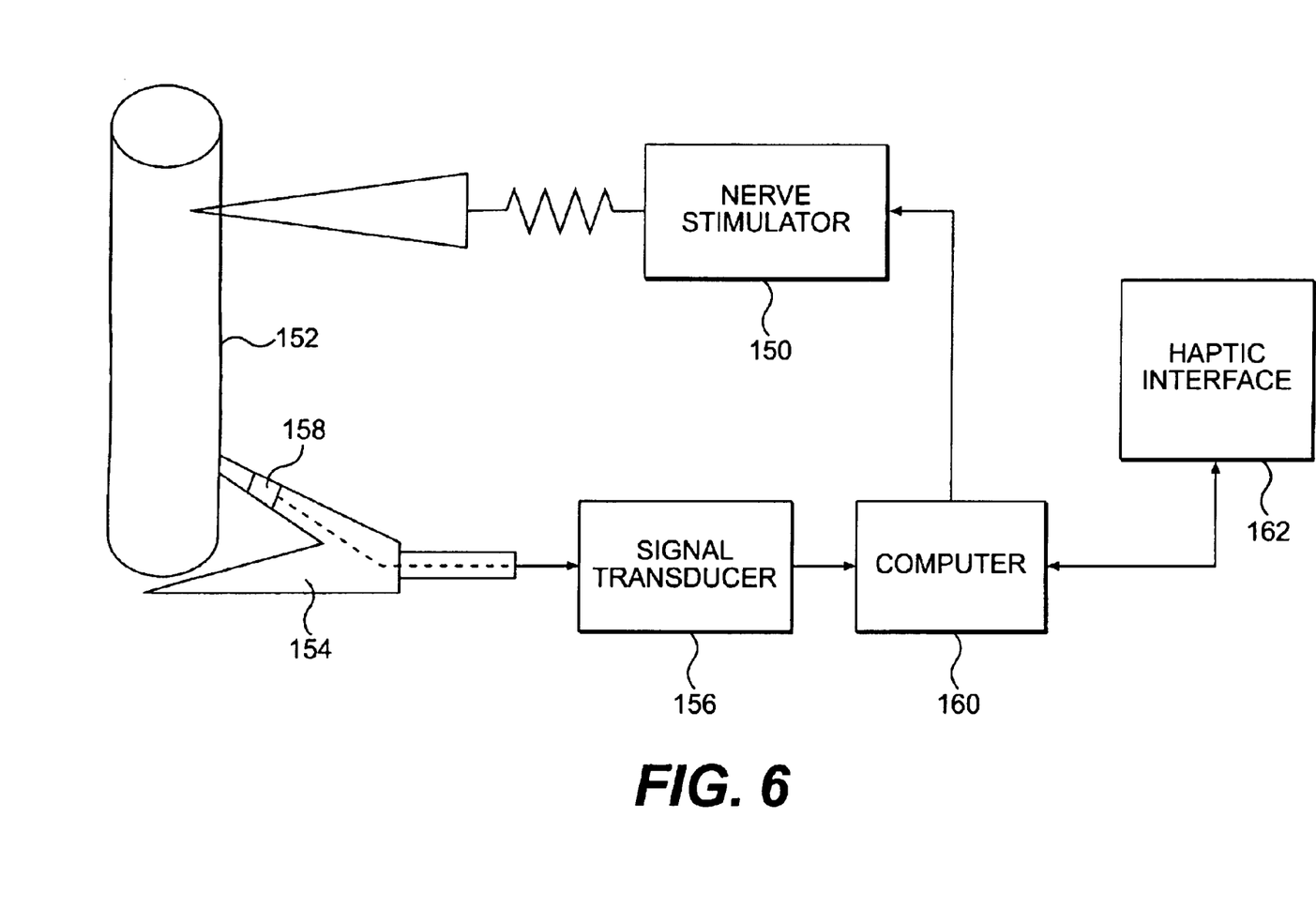
FIG. 6 is a schematic block diagram illustrating an alternative embodiment of the present invention employing a nerve stimulator.

Software algorithms may be used to identify certain electrical fields. In this way the electrical "signature" of a particular neurovascular bundle, such as the facial nerve or sensory nerves, can be discriminated from other neuro-electrical impulses. If no signature is present, e.g., due to denervation, then an ultra-low energy nerve stimulator may be employed. FIG. 6, which will be described in further detail hereinafter, illustrates a nerve stimulator for providing or enhancing a "signature".

A stimulator is capable of emitting a predefined specific repeating electrical signal created by a sensing computer. In this way the stimulator energy: 1) is kept below the threshold of injury to the nerve trunk and electrical trauma to the nerve is eliminated (conventional nerve stimulators may cause injury); and 2) an electrical "signature" is created to specifically identify the particular nerve. The sensing computer can thus identify specific nerve roots and trunks by the particular electrical pattern "signature" generated by the nerve stimulator.

With a unique electrical signature, a robot (for example) can then track the nerve or neurovascular bundle and establish an algorithm (mapping) to create a virtual wall around the structure, which is then used to prevent inadvertent transection or trauma to the structure. The electromagnetic signature of different neurovascular structures can be programmed into the robot used for a surgical dissection. As a result, a virtual conduit is placed around the neurovascular bundle such that the robot automatically dissects along this neurovascular bundle, tracking along the bundle to the target area (e.g., tumor, aneurysm, or other disease state) but does not transect the neurovascular bundle or deviate from the path of the bundle to other anatomical structures. This facilitates rapid surgical dissection in a relatively bloodless manner and ensures that no injury occurs to the nerves along the pathway.

In a similar manner, thermal sensors may be positioned at the tip of the surgical instrument to measure and relay subtle differences in temperature. These differences can discriminate, for example, an artery from a vein in neurovascular bundles on the extremities. A thermistor either amplifies the thermal signal, i.e., translate a 0.1° temperature as a 10° temperature, or translates the thermal signal into a palpable harness/softness or vibration signal using a piezoelectric crystal in the surgeon's haptic interface. Other critical structures such as the ureters can be flushed with warm saline solution to enhance temperature recognition. A software algorithm coupled to a thermistor may, for example, block a dissection in areas above a certain temperature. In this example, the ureters would feel "hard" relative to surrounding tissues, enabling the surgeon to avoid the ureters.

In a similar manner, a gamma-counter may be mounted to the tip of an instrument. Following injection of a radiolabled substance, dissection and sensing of the radioactivity proceed simultaneously. The degree of radioactivity may be mapped to a vibrational signal, tactily indicating to a surgeon proximity to a critical tissue site, (e.g., lymph node, abscess pocket or other radio-tagged tissue).

In the foregoing examples, reference has been made to the sensing of certain non-visible parameters for the purpose of providing real-time force or vibration feedback to the haptic interface. These same parameters may also be sensed, in either a sequential or scanning mode, and the values stored in order to establish a database, used subsequently for mapping a virtual image onto a display device.

Figure 1:
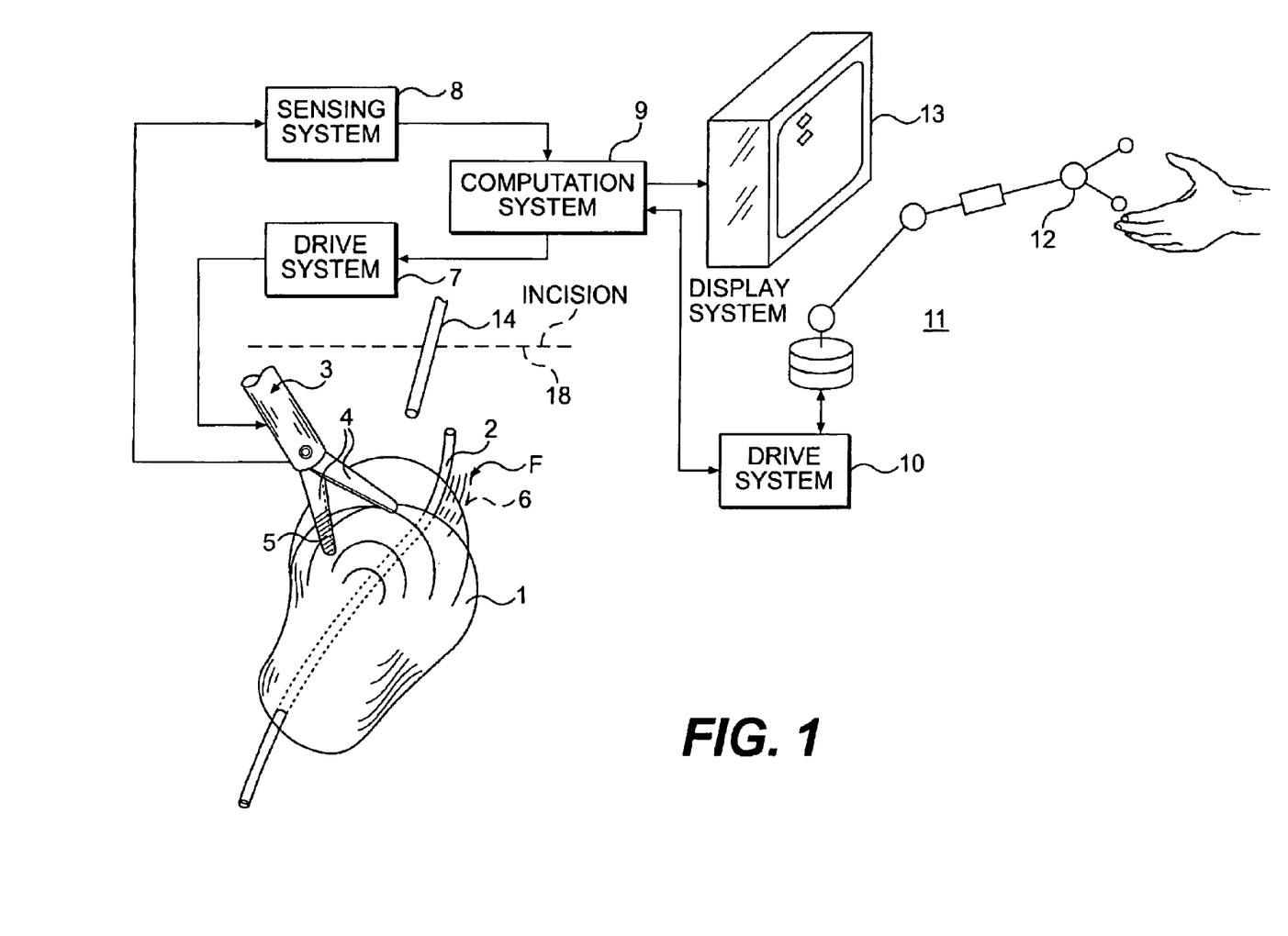
FIG. 1 is a schematic block diagram illustrating an embodiment of the present invention.
Figure 2:
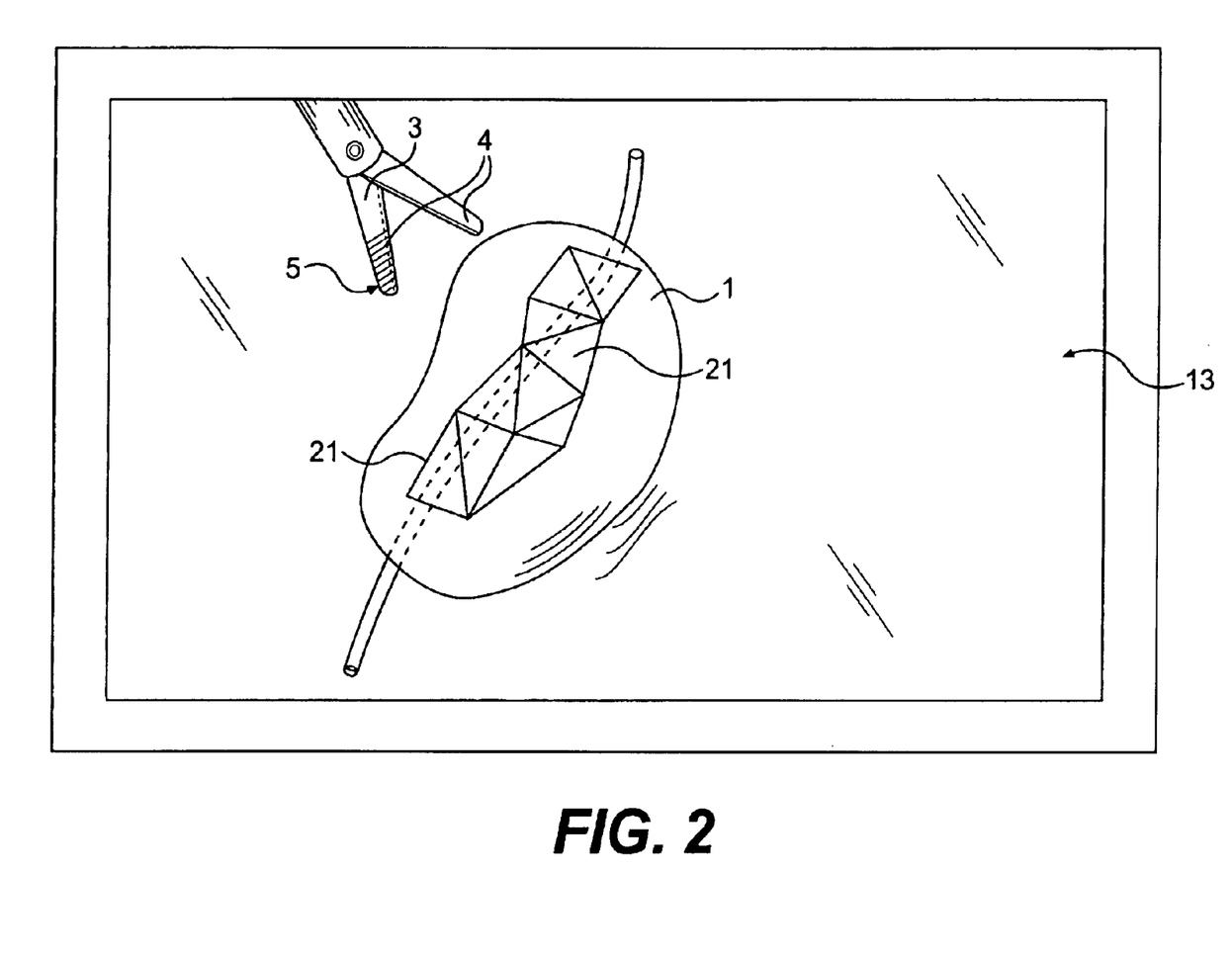
FIG. 2 is an embodiment of a visual display according to the present invention.

Reference is now made to the drawings, and in particular FIGS. 1 and 2. FIG. 1 illustrates a block schematic diagram of one embodiment of the present invention. FIG. 2 shows details of a visual display illustrating, by virtual field boundaries, the location of invisible structures.

FIG. 1 illustrates as a representative internal body site of interest a visible tissue 1 having extending therethrough a nerve 2. Although the nerve is shown in FIG. 1 it is generally not visible on the display 13. FIG. 1 shows the nerve 2 inside the tissue 1, in dotted outline to indicate the non-visible nature of the nerve.

FIG. 1 also illustrates the distal end of a surgical instrument 3 having a tool or end effector, such as the gripping jaws 4 illustrated in FIG. 1. An endoscope 14 is also shown proximate to the tissue 1. The endoscope 14 is shown extending through an incision 18 illustrated in dotted line in FIG. 1. The endoscope typically carries a camera for detecting a visual image at the tissue 1, which is shown on the display 13.

In FIG. 1, associated with the nerve 2, is an electric field F shown in dashed lines. This field is considered as a non-visible field. In this particular example it is an electric field but also, the sensing in accordance with the present invention can be thermal, radioactive, IR and other types of fields associated with anatomic structures, and including self-excited fields.

FIG. 1 shows a sensor 5 on the tool at the tip of the instrument 3. Here the sensor 5, in sensing the location of a nerve 2, may be a voltmeter or, more appropriately, a micro or millimeter range voltage meter. The output from the sensor 5 couples to a sensing system 8 which, in turn, couples to a computation system 9. A drive system 7 is coupled from the computation system 9 to the instrument 3 for the control of the operation of instrument 3.

Also depicted in FIG. 1 is display system 13 interconnecting with the computation system 9. A second drive system 10 couples to the computation system 9 and interfaces with a haptic interface 11. Adjacent the haptic interface, here an operating handle 12, is illustrated a surgeon's hand.

Thus, the surgeon can carry out manipulations at the haptic interface 11 in order to control, by way of drive system 10, computation system 9, and drive system 7, the instrument 3 conducting some medical procedure. The control may include multiple degrees-of-freedom of control of the instrument, one of which is opening and closing of the jaws or grippers 4. While the surgeon is carrying out such manipulations, there is a visual image of the tissue 1 on the display 13. However, this visual image does not include an image of the nerve 2 because this is essentially invisible on the display 13. However, in accordance with the invention by detecting the non-visible electrical field F, via the sensor 5, the computation system 9 can map the detected field to the display 13, as shown in FIG. 2.

FIG. 2 illustrates, on the display 13, a visual image of the tissue 1. The display also depicts a virtual image or boundary, designated by polygons 21, that correspond in position generally to the placement of nerve 2 within the associated tissue 1. In this way, if the end effector 4 is performing certain tasks associated with the tissue 1, including dissection of the tissue, the virtual image area represented by the polygons 21 may be avoided.

The virtual image area displayed in FIG. 2 may be developed by an operator manually moving the instrument 3 (and sensor 5) about an area proximate to the tissue 1. As the instrument/sensor is moved, different voltages are sensed relative to the field F as the end effector is moved from position to position. Alternatively, after the instrument is placed through the incision, movement of the instrument/ sensor could be controlled by a computer to transition about the tissue 1 in a sufficient number of locations so as to create a "map", and from that map, a database. If the instrument is under computer control, this control can be established in a predetermined pattern or it can be a form of random control. The computation system 9 may store (in a database) a field strength signal associated with each of the locations visited by the sensor as it is either moved by the surgeon or automatically under computer control. An algorithm of the computer system 9 then looks at the data and determines the boundaries, establishing the polygons 21 illustrated in FIG. 2. These represent areas to be avoided, in this particular example, as they overlie an area where a nerve appears and where dissection is not to occur.

The computation system 9 receives several pieces of data used in determining the content of the display 13. First, from the endoscope 14, a visual image data set is generated by digitizing the received optical pattern into well-known "pixels" representative of the whole area being looked at. These pixels can be stored on an up-dating basis by location and intensity, with intensity levels corresponding to each and every location being displayed to provide the actual (visual) image at the site of interest. Next, system 9 receives a signal from for example a location sensor identifying the location of the instrument end effector (and thus field sensor 5) at all times. The location of the end effector or tool is well-known in telerobotic systems, particularly as it relates to manipulations at the master haptic interface.

In addition, from the sensor 5 there is provided to computation system 9, for a plurality of sites, location and intensity of the detected non-visible field. In this example of using a voltmeter to detect electrical activity from a nerve or nerve bundle, by scanning the area of interest (either manually or under computer control) one can establish intensity levels for all sensed locations. These levels can be essentially overlayed on the visual image display as polygons 21 illustrated in FIG. 2. For example, the apex of each polygon may represent points of the same intensity. The polygons may be in the form of triangles of a size as depicted in FIG. 2, or may be smaller depending upon the resolution of the detection system.

The database contains stored values of the sensed parameter, as to location and intensity. If scanning was performed under computer control, there is a field strength stored for each location (pixel) visited during the scan. A control algorithm in computation system 9 then simply examines the database and determines boundaries, such as represented by the polygons 21 in FIG. 2. In a simple form, the algorithm may utilize threshold levels for demarcation. For example, levels over a certain predetermined value are highlighted. This highlighting could be by color variation or other indicia on the display, such as by establishing a "fog" or "blur" in those areas above the detected threshold.

There may be provided certain synchronization signals at the computation system 9 to control both the visual image and the virtual boundaries; such synchronization is within the knowledge of the person in the art. The display device 13 is typically controlled by synchronization signals and here there is simply a case of coordinating visual image signals with virtual image signals.

In addition to establishing a virtual image, the system may also provide feedback to the haptic interface 11. For example, as the sensor 5 gets closer to the nerve 2, the field strength increases. This measured strength, sensed by the sensor, is coupled by way pill of the sensing system 8 to the computation system 9, and from there to drive system 10 and haptic interface 11. This feedback can be used to indicate at the handle 12 that the distal end of the instrument 3 is approaching an area where there is a nerve, so that dissection should be avoided in that area This control is on a real-time basis.

Thus, as the surgeon manipulates the handle 12, if the instrument tip gets close to a nerve 2, there will be a feedback by way of the sensing system 8 so as to provide one or more of a vibration to the handle 12 and a force feedback to the handle 12 in order to inhibit or lessen further action at the end effector. If the end effector is a scalpel or scissors, this would impede or lessen further action and signal to the surgeon that he is in the vicinity of a nerve and must be careful to not cause a dissection of the nerve. This control may be exercised using threshold levels. Alternatively, the feedback may be provided as an audible alarm.

In connection with the system described in FIGS. 1 and 2, it is noted that the system operates so as to essentially "warn" a surgeon (provide an alarm) of proximity to a nerve or other critical anatomic structure (an avoidance area). This aspect of the invention also applies to establishing a "landmark", for example, so as to highlight or even to guide the instrument to the landmark area. As a further example, mention has been made previously to use of a gamma counter for sensing and locating a critical tissue site such as a lymph node. The sensed radioactivity can be used to pinpoint the location of this anatomic structure for the purpose of a surgical procedure.

Figure 3:
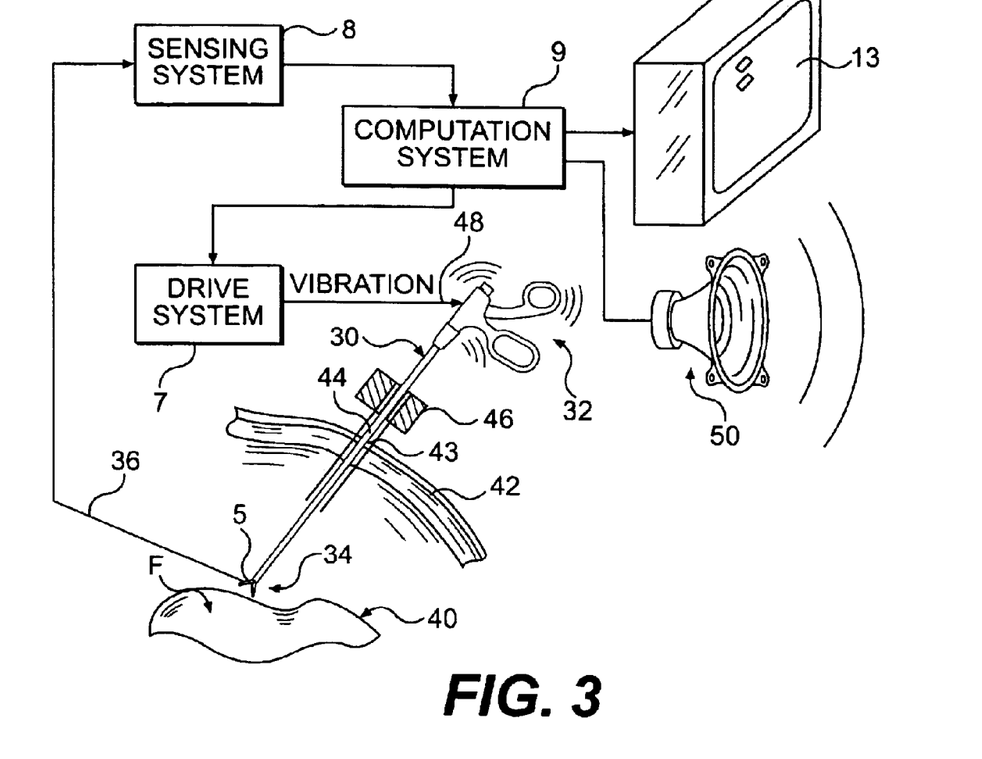
FIG. 3 is a schematic block diagram of an alternate system in accordance with the present invention, as applied to a hand-held instrument.

Reference is now made to the block schematic diagram of FIG. 3, disclosing an alternative embodiment utilizing a hand-held instrument. The instrument 30, which may be a laparoscopic instrument, has at one end an operating handle 32 (as the haptic interface) and at the other end an end effector 34. The end effector 34 is illustrated in proximity to a tissue 40. Associated with the end effector 34 is a sensor 5 that may be, for example, a voltmeter, thermistor or radioactive detector. A signal line 36 couples from the sensor to the sensing system 8.

FIG. 3 depicts an anatomic wall 42 having an incision 43 for receiving a shaft 44 of instrument 30. The instrument shaft may be guided through the incision by a trocar 46, as illustrated. Under normal operating conditions, the surgeon can manipulate the handle 32 to actuate the end effector 34 and can, under manual control, move the instrument in multiple degrees-of-freedom in carrying out a surgical procedure.

In addition to the sensing system 8, FIG. 3 also includes computation system 9 and drive system 7. In this embodiment the drive system 7 generates a control signal on line 48 for feeding back to the instrument 32 a vibration signal as an indication to the surgeon at the handle 32 that the end effector is coming into close proximity to a sensed non-visible field F. When the end effector 34 comes in sufficiently close proximity to the site having the associated field F, the sensing system 8 senses this condition and the computation system 9 along with drive system 7 causes a signal on line 48 to create a vibration at the handle 32. The magnitude of the vibration may be a function of the proximity of the end effector to the field. As in the previous example given, the field may be generated from a nerve or nerve bundle. FIG. 3 also illustrates an alternate form of feedback to the surgeon, where the computation system 9 has an output coupling to an audio speaker 50 for providing an audible signal to the surgeon of a proximity of the end effector to the aforementioned field.

Figure 4:
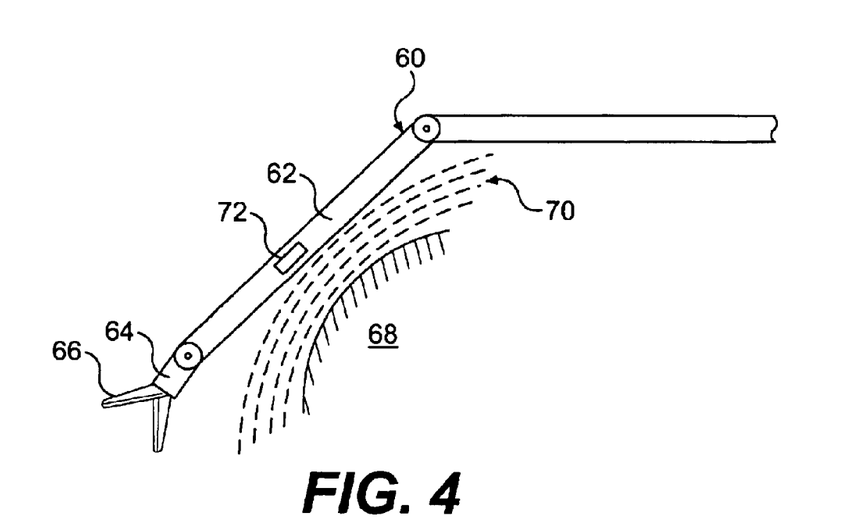
FIG. 4 is a schematic diagram illustrating an alternate embodiment of a device for locating a sensor.

In FIGS. 1–3, the sensor is disposed at the very tip of the instrument, more specifically at the end effector. However, in accordance with other embodiments the sensor may be disposed at other positions on the instrument, or could even be at a position other than on the instrument. In this regard, FIG. 4 shows a portion of an instrument 60 having an arm 62, a wrist section 64 and end effector 66. The instrument 60 is illustrated in proximity to a tissue 68 that may be considered as having a nerve or nerve bundle close to its surface emanating a non-visible field F 70. The arm 62 is carrying a sensor 72 at a predetermined position along the arm. Here, the purpose may be to avoid having the arm 62 contact the tissue 68. By disposing the sensor 72 on the arm 62, a feedback signal can be provided to the surgeon as to the proximity between the instrument arm 62 and the tissue 68.

The mapping aspect of the present embodiments relate to the translation of certain sensed parameters into actions or displays for improved surgeon control of certain surgical procedures. The control can be provided by giving the surgeon an improved display to observe as he operates, a visual image along with a virtual image as described herein. The control may also include feedback to the haptic interface to provide the surgeon with tactile or audible feedback based upon sensed non-visible parameter.

Figure 5:
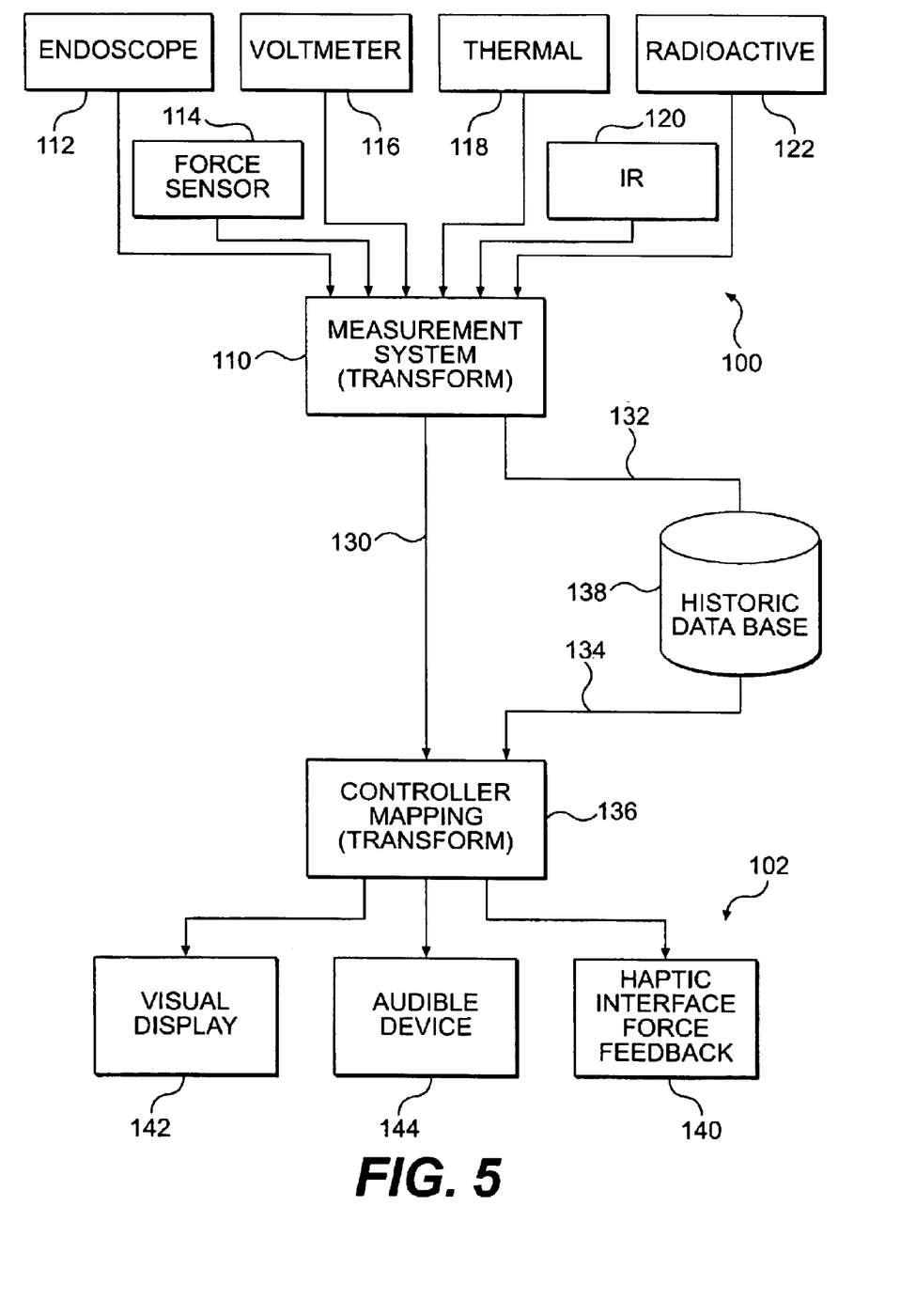
FIG. 5 is a block diagram illustrating various relationships between sensed parameters, transformed data and signals, and applied outputs, according to various embodiments of the present invention.

Various mapping or translation techniques are illustrated in the block diagram of FIG. 5. FIG. 5 shows a sensing side at 100 and a display or control side at 102. Various system blocks extend between these two sides to provide the mapping. Specific examples follow hereinafter. It is understood that systems can be readily designed that incorporate only some of the blocks shown in FIG. 5.

On the sensor side 100 of FIG. 5 there are depicted a number of different sensing devices, each coupling to a measurement and transform system 110. Often, only one sensor is employed in a specific embodiment. These sensors include an endoscope 112, a force sensor 114, a voltmeter 116, a thermal sensor 118, an IR detector 120, and a radioactive detector 122. The endoscope 112 can provide a visual image (at display 142) of the anatomic body site of interest. The force sensor 114 may be any well-known type of force sensor that provides an indication of a contact force when disposed for example at the end effector of the instrument. The other sensors 116, 118, 120 and 122 are non-contact and non-visible field sensors. The voltmeter 116 may comprise a milli-voltmeter or micro-voltmeter. The thermal sensor 118 may include a thermistor. The radioactive detector 122 may comprise a gamma counter.

In FIG. 5, the measurement system 110 may provide some type of signal transformation or processing. Multiplexing may be provided to handle the various sensed signals. Two basic data paths are shown connecting from the output of the measurement system 110—one path at line 130 to controller 136 that represents current ("real time") sensed data from one of the sensors, and another path at line 132 to database 138 that represents data, over time, to be stored in the historic database 138. The output of database 138 also couples via line 134 to controller 136. The controller 136 couples to and controls devices such as the illustrated visual display 142, audible device 144, and haptic interface force feedback device 140.

In FIG. 5 the side 100 may be considered as the slave side or station, while the side 102 may be considered as the master side or station. Thus, in FIG. 5 there is shown at side 102 a haptic interface which has the ability of receiving tactile (force or vibration) feedback signals indicative of the sensing of certain fields at the slave side. Also illustrated in FIG. 5 is the visual display 142 and the audible device 144.

In FIG. 5, one or both of the controllers 110 and 136 provide the signal mapping and contain one or more pre-stored algorithms to determine virtual boundaries (polygons 21) from the historic data in the database 138. The controller (s) also control feedback to the haptic interface 140, such as from the sensors, and may or may not take into account historic data. Of course, the controller(s) also control action initiated by the operator at the haptic interface to the instrument.

In FIG. 5 there may also be applied certain modeling techniques. These may be considered as applied at one or more of the controllers 110 and 136. Modeling techniques can be used to transform data at the master side based upon certain established models. For example, modeling may be used to account for tissue movements based upon instrument actions. Modeling may be particularly advantageous for anatomic sites where it is anticipated that tissues or organs may move upon interaction with the surgical instrument. This involves spatial modeling. There may also be circumstances, such as are involved in cardiac procedures, when temporal modeling can be applied. Models may be used that account for both special and temporal parameters. A force feedback from a force sensor (see FIG. 5) may be used as a control element in controlling the finite element modeling. In temporal modeling the control algorithm may be based primarily on an EKG waveform.

In other embodiments of the invention, rather than using only one type of sensor for performing a particular procedure, multiple sensors may be employed. These multiple sensors could be supported on an instrument carrying one or more end effectors, or could be supported together on a separate instrument or probe. Alternatively, each sensor could be supported by its own probe or instrument. For example, in performing a sentinel node biopsy, a first sensor may be used to establish a virtual image of pertinent artery, vein and nerve structures, and a second sensor may be used to detect radio activity at the pertinent mode, thus generating a second virtual image or boundary of the node location. These virtual images may be overlayed in a visual display to assist the surgeon in quickly and reliably carrying out the surgical procedures.

The sensing that is employed, such as in association with nerves or nerve bundles, typically relies upon an inherent electric field disposed about the nerve or nerve bundle. However, there may be circumstances in which such a field is not of a sufficient strength. Thus, in the embodiment of FIG. 6, there is added to the system a nerve stimulator 150. FIG. 6 schematically illustrates a nerve 152, a gripper 154 or other end effector construction, and a signal transducer 156 coupled with the gripper and receiving signals from a sensor 158 disposed on one of the grippers. The signals that are outputted from the signal transducer 156 couple to a control computer 160 that also interfaces with the haptic interface 162.

The system of FIG. 6 employs an ultra-low energy nerve stimulator 150. The stimulator is capable of emitting a predefined specific and preferably repeating electrical signal that is controlled from the computer 160. The output of the stimulator 150 is kept below the threshold of injury to the nerve trunk 152. This eliminates any electrical trauma to the nerve. Furthermore, this system creates an electrical "signature" to specifically identify the particular nerve construction. The sensing computer 160 can thus identify specific nerve roots and trunks by the particular electrical pattern "signature" generated by the nerve stimulator 150.

The following are further examples of various aspects of the invention. Several examples of different mapping concepts are set forth, supported by descriptions found in FIGS. 1–6. These mapping concepts may be practiced in either a robotic or non-robotic system.

Mapping Visible Data to Haptic Interface

This may be embodied in a medical system comprising a sensing device for obtaining a visual image of an anatomic body site, a surgical implement, and a manipulator controllable by a surgeon for control of the surgical implement at the anatomic body site. The sensing device may comprise the endoscope 112 illustrated in FIG. 5. The manipulator may be the one illustrated in FIG. 1. The system includes a controller, such as the controller 136 in FIG. 5. The controller intercouples the sensing device and the manipulator and includes a mapping component for translating predetermined characteristics of the visual image into a signal for controlling action at the manipulator. For example, there may be certain aspects of the visual image in which the visual data is synthesized to identify certain locations of the visual display that are to be highlighted and thus avoided by the surgeon. When the instrument is at these locations then the controller provides a force feedback signal to the manipulator, or haptic interface 140 illustrated in FIG. 5. The feedback signal may be in the form of a tactile or audible signal. Preferably, the feedback signal is a signal that the surgeon "feels" (tactile) at the haptic interface essentially signaling to the surgeon that the instrument is at an area that is to be avoided. This feedback to the haptic interface may supplement the surgeon's actual direct viewing of a display, such as the display 142 illustrated in FIG. 5 or the display 13 illustrated in FIG. 1.

Accordingly, this type of mapping identifies certain characteristics of the visual display, typically through an endoscope, and converts the sensed data to a feedback control signal at the haptic interface. The parameters that are identified on the display may be, for example, arteries, veins or other anatomic structures. Even though these structures may be visible to the surgeon through the display, there is an added advantage of providing this feedback to the haptic interface to supplement what the surgeon views at the display.

This form of mapping identifies visual boundaries such as by differences in contrast or gray scale and converts these boundaries to transition locations where signals are fed back to the master interface to signal (to the surgeon) areas that are to be avoided or targeted.

Mapping Visible Data to Vibration

Such a medical system may employ many of the same components as discussed with regard to the mapping of visual data to a haptic interface. However, instead of a feedback signal at the haptic interface, the control signal may be provided to the manipulator and comprise a vibration signal. In this regard, FIG. 3 shows a vibration signal on line 48 coupling from drive system 7 to manipulator (handle) 32. The only difference here is that in FIG. 3 one is sensing a non-visible field, while in this example one is providing a vibration signal based upon sensing a visual field.

Mapping Visible Data to Audible Device

This may be embodied in a medical system that comprises a sensing device for obtaining a visual image of an anatomic body site, a surgical implement and a manipulator controlled by a surgeon for control of the surgical implement at the anatomic body site. The system also includes an audible device. The sensing device may be the endoscope 112 in FIG. 5. The manipulator may be the haptic interface 11 in FIG. 1. The audible device may be device 144 in FIG. 5. The medical system also includes a controller, such as controller 136 in FIG. 5. This controller intercouples the sensing device and the audible device and includes a mapping component for translating predetermined characteristics of the visual image into a signal for controlling the audible device.

Accordingly, in this form of mapping, certain characteristics of the visual image are interpreted by the controller and if the instrument goes within identified locations, an audible alarm is activated. This indicates to the surgeon that the instrument is approaching or within a zone of the anatomic body site where either the surgeon has to be more careful or that should be avoided. Alternatively, the alarm may identify an area to be targeted.

The predetermined characteristics of the visual signal may represent an outline of an anatomic body member. The controller controls the audible device as a function of the position of the surgical implement within the anatomic body site and relative to the anatomic body member. The audible device is sounded when a surgical implement comes within a predefined proximity to the anatomic body member, so as to signal that, for example, the surgical implement is too close thereto.

Mapping Force Sensor to Visual Display

A medical system that embodies this mapping concept may comprise a surgical implement, a manipulator controlled by an operator for control of the surgical implement at an anatomic body site, and a force sensor for detecting a force imposed on the surgical implement at the anatomic body site. Refer to FIG. 5 for a force sensor 114. Such a medical system may also include a visual display observable by the operator and a controller, such as controller 136 of FIG. 5 that intercouples the force sensor and visual display. The controller includes a mapping component or block for translating predetermined characteristics from the force sensor into a signal for controlling the content of information of the visual display. The controller controls the display content as a function of the position of the surgical implement within the anatomic body site. Preferably the force sensor is carried at the tip end of the surgical implement. The controller is responsive to a force signal from the force sensor for highlighting an area of the visual display corresponding to a location of the surgical implement.

In accordance with this form of mapping, an area on the display can be "highlighted" to indicate an area where the detected force has exceeded a predetermined threshold. Such mapping may be employed on a "real time" basis or the surgical implement may be moved by the surgeon throughout an anatomic body site, or under computer control to generate a map of forces that are detected. This map may then be illustrated on the display in a variety of different ways such as by the use of a contrasting color, a "flashing" on the display, or the use of other indicia on the display such as illustrated in FIG. 2.

Mapping Force Sensor to Vibration

A medical system embodying this form of mapping may comprise a surgical implement, a manipulator controlled by an operator for control of the surgical implement at an anatomic body site, and a force sensor for detecting a force imposed on the surgical implement at the anatomic body site. A controller intercouples the force sensor and the manipulator and includes a mapping block for translating predetermined characteristics from the force sensor into a signal for controlling vibration at the manipulator. Again, reference may be made to FIG. 3 showing a feedback vibration signal. In accordance with this form of mapping the vibration signal may be activated in accordance with the output of the force sensor.

The controller controls the manipulator as a function of the position of the surgical implement within the anatomic body site. The force sensor may be carried at the tip of the surgical implement. The controller is responsive to a force signal from the force sensor for controlling the manipulator as a function of the measured force level.

A force sensor map may also be developed by the surgeon moving the surgical implement with its mounted sensor about an anatomic body site, or by creating movement by way of computer control. This can establish a gradient over an anatomic body site of force levels that can be used to control, via the controller, the vibration signal coupled to the manipulator.

Mapping Force Sensor to Audible Device

A medical system embodying this type of mapping may comprise a surgical implement, a manipulator controlled by an operator for control of the surgical implement at an anatomic body site, and a force sensor detecting a force imposed on the surgical implement at the anatomic body site. This system also includes an audible device such as the device 144 shown in FIG. 5 and a controller, such as a controller 136 shown in FIG. 5. The controller intercouples the force sensor and the audible device and includes a mapping block for translating predetermined characteristics from the force sensor into a signal for controlling the audible device. The controller is responsive to a force signal from the force sensor for controlling the magnitude of the audible signal from the audible device as a function of the magnitude of the force signal. The audible signal may be generated only when the force signal exceeds a predetermined threshold or the audible signal may have an output magnitude that directly or inversely relates to the force signal magnitude.

In accordance with this form of mapping, a detected force signal is coupled to the controller and from there to an audible device to indicate an audible signal to a surgeon when a predetermined force is sensed. This preferably occurs in "real time".

Mapping Non-Visible Field to Visual Display

A medical system that embodies this mapping concept may comprise a surgical implement, a manipulator controlled by an operator for control of the surgical implement at an anatomic body site and a sensing device for sensing a non-visible field generated from an anatomic body structure disposed within the anatomic body site. The system may also include a visual display and a controller. With regard to the sensing device, reference is made to FIG. 5 illustrating a number of different forms of sensing devices for measuring the non-visible field. The controller intercouples the sensing device and the visual display and includes a mapping block (see FIG. 5 and controller 136) for translating predetermined characteristics of the non-visible field from the sensing device into a signal for controlling the content on the visual display.

The manipulator, such as the handle 12 illustrated in FIG. 1 as part of the interface 11, intercouples with the computation system 9 in FIG. 1. The controller is responsive to actions at the manipulator to control the surgical implement in performing a surgical procedure. The controller establishes on the display both a visual image of the area at the anatomic body site as well as a virtual image representative of a boundary defined by the mapping block. The polygons 21 in FIG. 2 illustrate a boundary on the visual display representative of an area that is actually invisible to the surgeon observing the display (such as display 13 illustrated in FIG. 1).

The non-visible field may be any one or more of a variety of fields. Refer to FIG. 5 and inputs to the measuring system 110 such as the voltmeter 116, thermal sensor 118, IR detector 120 or radioactive detector 122. Thus, these fields may be, but are not limited to, electrical, electromagnetic, thermal, radioactive or an IR field.

This mapping enables the sensing of parts of anatomic structures that are not directly visible to the surgeon. This mapping enables a conversion of a non-visible field, into a visible (virtual) boundary on a display that the surgeon is observing. This boundary, such as that illustrated in FIG. 2 by the polygons, is essentially a virtual conduit that is placed about the anatomic structure such as a neurovascular bundle. In this way, the surgeon can control dissection so that it occurs outside of and along these neurovascular bundles, tracing along the bundle to the target area without any transection of the neurovascular bundle. This facilitates rapid surgical dissection in a relatively bloodless manner and that insures no injury occurs to the nerves along the pathway.

Mapping Non-Visible Field to Haptic Interface

A medical system that embodies this mapping may comprise a surgical implement, a manipulator controlled by an operator for control of the surgical implement at an anatomic body site, and a sensing device for sensing a non-visible field generated from an anatomic body structure disposed within the anatomic body site. Suitable sensing devices are illustrated in FIG. 5. A controller intercouples the surgical implement, manipulator and sensing device and includes a mapping block for translating predetermined characteristics of the non-visable field from the sensing device into a signal for controlling actions at the manipulator. The signal for controlling actions usually controls a tactile feedback to the operator.

In accordance with this form of mapping non-visible fields are sensed. A feedback occurs to the master interface to feedback a tactile signal to the surgeon indicating that the instrument is now at a location that corresponds with a certain field intensity. This form of tactile feedback is carried out preferably in "real time".

Mapping Non-Visible Field to Vibration

A medical system that embodies this form of mapping may comprise a surgical implement, a manipulator controlled by an operator for control of the surgical implement at an anatomic body site, and a sensing device for sensing a non-visible field generated from an anatomic body structure disposed within the anatomic body site. A controller is provided intercoupling the surgical implement, manipulator and sensing device and includes a mapping block for translating predetermined characteristics of the non-visible field from the sensing device into a vibration signal coupled to the manipulator.

Mapping Non-Visible Field to Audible Device

A medical system embodying this form of mapping may comprise a surgical implement for carrying out a predetermined surgical procedure at an anatomic body site, a sensing device for sensing a non-visible field generated from an anatomic body member disposed within the anatomic body site, and an audible device. The audible device is illustrated as device 144 in FIG. 5 and the sensing device may be the sensing devices illustrated in the block diagram of FIG. 5. A controller, such as controller 136 in FIG. 5 intercouples the sensing device and the audible device and includes a mapping block for translating predetermined characteristics from the sensing device into a signal for controlling the audible device. The controller is responsive to the magnitude of the sensed field for controlling the audible signal as a function of the magnitude of the sensed field.

With regard to the mapping, FIG. 2 shows polygons that demarcate an area of an underlying invisible structure. Where this anatomic structure is a nerve or nerve bundle, detection of an electric field associated with the nerve or nerve bundle can be accomplished by "scanning" so as to establish the map and the polygons illustrated in FIG. 2. This scanning can occur by virtue of the surgeon moving the surgical instrument about the anatomic body site with the controller detecting successive positions, storing these positions and establishing a map from the stored values based upon the intensity of the signal. Alternatively, this mapping may occur automatically under computer control.

Reference has been made to medical and surgical implements and instruments. Catheters or any other type of medical instrumentation or guide device can be used in accordance with the present invention.

Another system for computer-controlled manipulation of a medical instrument, which may be useful in various embodiments of the present invention, is described in U.S. Pat. No. 6,197,017, issued Mar. 6, 2001 to Brock and Lee, entitled "Articulated Apparatus for Telemanipulator System," which is also incorporated by reference in its entirety.

Having now described a number of embodiments of the present invention, it should be apparent to those skilled in the art that numerous other embodiments and modifications thereof are contemplated as falling within the scope of the present invention, as defined by the appended claims.

What is claimed is:

1. A system for generating a display of a body structure and for providing haptic feedback to a medical practitioner, said system comprising:

a master station that includes a user interface;

a slave station that includes a medical implement;

a sensor on the medical implement positionable at an internal body site for sensing a non-visible field of a body structure at the site;

a measurement system responsive to said sensor for providing a sensor signal indicative of the field strength;

a controller intercoupling the master and slave stations and responsive to manipulations at the user interface by said medical practitioner to control said medical implement;

said controller transforming the sensor signal into virtual image data representative of the body structure;

a source of visual image data for the site; and a display system enabling combined display of the visual image data and the virtual image data for observation by the medical practitioner at the master station;

said controller transforming the sensor signal into a tactile feedback signal, said user interface receiving said feedback signal for providing a tactile response to the medical practitioner at the user interface.

2. The system of claim 1, wherein the non-visible field is at least one of an electrical field, a thermal field, an infrared field and a radioactive field.

3. The system of claim 1, wherein the sensor is at least one of a voltage sensor, a thermal sensor, an infrared sensor, and a radioactive sensor.

4. The system of claim 1, wherein the sensed field is associated with at least one of a nerve, nerve bundle and vascular vessel.

5. The system of claim 1, further including:

a stimulator emitting a stimulation signal for at least one of enhancing and generating the field.

6. The system of claim 5, wherein the stimulator emits at least one predefined stimulation signal for an associated body site.

7. The system of claim 1, wherein the controller includes, for at least one select site, an associated signature value of the virtual image data.

8. The system of claim 1, wherein the virtual image data defines a boundary of the field.

9. The system of claim 1, wherein the magnitude of the tactile response is a function of the magnitude of the sensor signal.

10. The system of claim 1, wherein the sensor is disposed at a distal end of the medical implement.

11. The system of claim 10, wherein the medical implement includes a tool used to perform a medical procedure at the site.

12. The system of claim 1, further including:

a hand-engageable user interface providing input to a computer for positioning of the implement.

13. The system of claim 1, wherein the controller includes: modeling data for associating the virtual image data with locations at the site.

* * * * *